United States Patent [19]

Suh et al.

[11] 4,440,941
[45] Apr. 3, 1984

[54] AROYL-AMINOACIDS, AMIDES AND ESTERS THEREOF

[75] Inventors: John T. Suh, Greenwich, Conn.; Paul R. Menard, Tuckahoe, N.Y.; Howard Jones, Holmdel, N.J.

[73] Assignee: USV Pharmaceutical Corporation, Tarrytown, N.Y.

[21] Appl. No.: 219,051

[22] Filed: Dec. 22, 1980

[51] Int. Cl.³ .................... C07C 63/04; C07C 69/84
[52] U.S. Cl. ........................ 560/20; 560/22; 560/41; 562/494; 562/450; 564/154; 564/155; 564/162; 546/176; 424/308; 424/317; 424/324
[58] Field of Search ............ 564/162, 154, 155; 560/20, 22, 41; 562/444, 450

[56] References Cited

U.S. PATENT DOCUMENTS

| | | | |
|---|---|---|---|
| 2,603,617 | 5/1952 | Hook et al. | 564/162 |
| 2,895,992 | 7/1959 | Ohnacker et al. | 564/162 |
| 3,177,252 | 4/1965 | Thominet | 564/162 |

*Primary Examiner*—Paul M. Coughlan, Jr.
*Assistant Examiner*—D. B. Springer

[57] ABSTRACT

Compounds of the structure

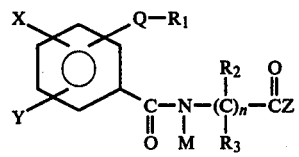

wherein:
Q is oxygen, sulfur or imino.
X and Y are hydrogen, halogen, hydroxy, alkoxy, trifluoromethyl, nitro, carboxy, cyano, sulfonamido, sulfhydryl, alkyl, alkenyl, alkynyl, alkanoyl, alkylmercapto, amino, alkylamino, dialkylamino, alkysulfinyl, and alkylsulfonyl and may be the same or different;
$R_1$ is hydrogen, alkanoyl, substituted alkanoyl wherein the substituent is hydroxy, amino or cycloalkyl, aroyl, arylalkanoyl, or cycloalkylcarbonyl,
n is an integer from 1 to 4 inclusive,
$R_2$ and $R_3$ are hydrogen, alkyl, alkenyl, alkynyl, cycloalkyl, cycloalkyl-alkyl, aryl, aralkyl, and substituted derivatives thereof wherein the substituents are hydroxy, amino, alkylamino, dialkylamino, alkoxy, halogen, hydroxy, mercapto, alkylmercapto and nitro, and may be the same or different;
M is alkyl, alkenyl, alkynyl, cycloalkyl, cycloalkylalkyl, aryl, aralkyl, and hetero; and
Z is hydroxy, amino, alkylamino, dialkylamino, or alkoxy,
have angiotensin converting enzyme inhibitory activity.

12 Claims, No Drawings

AROYL-AMINOACIDS, AMIDES AND ESTERS THEREOF

This invention relates to new chemical compounds possessing valuable pharmaceutical activity. It particularly relates to compounds possessing antihypertensive and angiotensin converting enzyme inhibitory activity and having the structure:

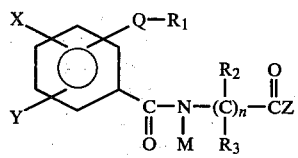

wherein:

Q is oxygen, sulfur or imino;

X and Y are hydrogen, halogen, hydroxy, alkoxy, trifluoromethyl, nitro, carboxy, cyano, sulfonamido, sulfhydryl, alkyl, alkenyl, alkynyl, alkanoyl, alkylmercapto, amino, alkylamino, dialkylamino, alkylsulfinyl, and alkylsulfonyl and may be the same or different;

$R_1$ is hydrogen, alkanoyl, substituted alkanoyl wherein the substituent is hydroxy, amino or cycloalkyl, aroyl, arylalkanoyl, or cycloalkylcarbonyl, n is an integer from 1 to 4 inclusive, $R_2$ and $R_3$ are hydrogen, alkyl, alkenyl, alkynyl, cycloalkyl, cycloalkyl-alkyl, aryl, aralkyl, and substituted derivatives thereof wherein the substituents are hydroxy, amino, alkylamino, dialkylamino, alkoxy, halogen, hydroxy, mercapto, alkylmercapto and nitro, and may be the same or different;

M is alkyl, alkenyl, alkynyl, cycloalkyl, cycloalkylalkyl, aryl, aralkyl, and hetero; and Z is hydroxy, amino, alkylamino, dialkylamino, or alkoxy, and where Z is hydroxy, their nontoxic, pharmaceutically acceptable alkali, alkaline-earth, and amine salts.

The alkyl, alkenyl and alkynyl groups and the alkyl moieties in alkoxy, alkanoyl, alkylmercapto, alkylamino, dialkylamino, alkylsulfinyl and alkylsulfonyl contain from 1 to 6 carbon atoms. Such groups include methyl, ethyl, propyl, isopropyl, butyl, isobutyl, amyl, isoamyl, hexyl, vinyl, allyl, propenyl, ethynyl, propynyl, and the like.

The cycloalkyl groups preferably contain 3 to 7 carbon atoms.

The aryl groups contain from 6 to 10 carbon atoms and include phenyl, tolyl, xylyl, naphthyl and the like. The aralkyl groups may contain from 7 to 16 carbon atoms and include benzyl, phenethyl, naphthylmethyl, and the like. The aryl and aralkyl groups may carry substituents such as those listed in X and Y.

The hetero groups may be saturated and unsaturated and include pyrrolidyl, piperidinyl, morpholinyl, pyridyl, quinolinyl, furyl, furfuryl, thienyl, and the like.

The preferred compounds are those wherein X and Y are hydrogen, alkyl, halogen, trifluoromethyl and alkoxy, $R_1$ is hydrogen or alkanoyl, n is 1, Z is hydroxy, and Q is sulfur and is attached to the ring in a position ortho to the amide substituent.

Where Z is hydroxy, the suitable salts include the sodium, potassium, ammonium, and calcium.

The compounds of this invention may be readily prepared in accordance with the following reactions:

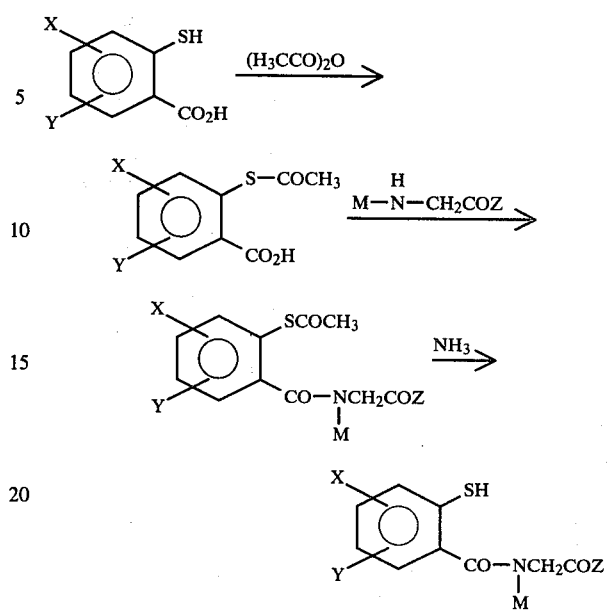

The desired starting materials and intermediates can be prepared from readily available materials using standard organic reactions. Modifications in X, Y, $R_1$, M, Z and n can be made as desired.

It is known to those skilled in the art that those compounds of the present invention having asymmetric carbon atoms may exist in racemic or optically active forms. All of these forms are contemplated within the scope of the invention.

The invention will be more fully illustrated in the examples which follow. These examples are given by way of illustration and are not to be considered as limiting.

Example I

A. 2-Acetylthiobenzoic acid

A mixture of 2-mercaptobenzoic acid (5.4 g, 35 mmol) acetic anhydride (4.3 g, 42 mmol) and acetic acid (15 ml) was refluxed 15 minutes. After cooling to room temperature the solution was poured into dilute hydrochloric acid. The product was filtered and recrystalized from toluene, m.p. 127°–129° C.

B. N-(2-Acetylthiobenzoyl)-N-cyclopentylglycine

N,N$^1$-Dicyclohexylcarbodiimide (15.9 g, 77 mmol) in methylene chloride was added slowly to a mixture of 2-acetylthiobenzoic acid (15.2 g, 77 mmol) and N-cyclopentylglycine t-butyl ester (15.4 g) in methylene chloride maintained at 0°–5°. The mixture was brought to room temperature overnight, filtered, and the filtrate washed successively with dilute hydrochloric acid, saturated sodium bicarbonate and saturated sodium chloride solutions. After drying, the organic portion was concentrated, the residue dissolved in ether and the resulting solution filtered. Concentration of the filtrate gave crude N-(2-acetylthiobenzoyl)-N-cyclopentylglycine t-butyl ester as an oil.

The crude ester (28.2 g) was combined with sodium iodide (16.5 g, 0.11 m) in acetonitrile (100 ml) and the mixture brought to 45° C. Chlorotrimethylsilane (11.9 g, 0.11 m) was introduced and heating was continued at 45°–52° for 26 min. The mixture was cooled, quenched with water (60 ml) and diluted with methylene chloride. The organic layer was removed, washed with water, sodium thiosulfate solution and brine, and concentrated in vacuo. Treatment of the residue with saturated sodium bicarbonate solution was followed by filtration of insoluble matter. The filtrate was washed with ethyl acetate, acidified (concentrated hydrochloric acid) and extracted (ethyl acetate). Drying and concentration of the extracts gave a residue which was purified by column chromatography or HPLC. The product was isolated as an amorphous solid.

Example II

N-(2-Mercaptobenzoyl)-N-cyclopentylglycine

Ammonia gas was bubbled through a solution of N-(2-acetylthiobenzoyl)-N-cyclopentylglycine (5 g, 15 mmol) in methanol (150 ml) for 70 minutes at room temperature. After stirring an additional 20 minutes the solution was concentrated in vacuo and the residue then partitioned between ethyl acetate (200 ml) and 5% sodium bisulfate solution (100 ml). The organic phase was removed, washed with sodium bisulfate solution and brine, then dried and concentrated. Column chromatographic purification of the residue followed by recrystallization from ethyl acetate afforded the white crystalline product, m.p. 148.5°–150° C.

Example III

A. 3-Trifluoromethyl-2-aminobenzoic acid

7-Trifluoromethylisatin (10 g, 46 mmol) was dissolved in 5% sodium hydroxide solution (83 ml). To this was added dropwise over 30 minutes a solution of 50% hydrogen peroxide (7.4 ml) in water (4.6 ml); the temperature rose to 50°. The solution was stirred an additional 30 minutes, acidified (conc. HCl) to pH 1–2, and the tan product was filtered.

B. 2-Mercapto-3-trifluoromethylbenzoic acid

3-Trifluoromethyl-2-aminobenzoic acid (8.8 g, 43 mmol) was added to a solution of sodium hydroxide (1.8 g, 45 mmol) in water (50 ml), followed by sodium nitrite (3.0 g, 43 mmol). The resulting brown suspension was added dropwise to a mixture of concentrated hydrochloric acid (11.8 ml) and ice (20 g) which was set in an ice bath. Stirring at 0° was continued for 30 minutes followed by filtration. The filtrate, being kept cold, was added dropwise to a cooled (0°–5°) solution of sulfur (1.5 g, 46 mmol), sodium sulfide nonahydrate (12 g, 50 mmol), sodium hydroxide (1.7 g, 43 mmol) and water (20 ml). After overnight stirring the mixture was filtered and acidified (concentrated hydrochloric acid) to yield the crude disulfide. This was collected by vacuum-filtration, being pressed as dry as possible.

The moist disulfide was refluxed with zinc (3 g, 45 mmol) and glacial acetic acid (100 ml) for 4 hours, an additional portion of zinc (3 g, 45 mmol) being added one hour after reflux began. The mixture was cooled and filtered, and the filter cake extracted several times with hot dilute sodium hydroxide solution. Acidification of the extracts with concentrated HCl gave a white powder which was not purified further.

C. 2-Acetylthio-3-trifluoromethylbenzoic acid

2-Mercapto-3-trifluoromethyl-benzoic acid (4.0 g, 18 mmol), acetic anhydride (2.2 g, 22 mmol), and glacial acetic acid (6 ml) were refluxed 30 minutes, cooled and combined with dilute hydrochloric acid, thereby affording the product as a white crystalline solid.

D. N-(2-Acetylthio-3-trifluoromethylbenzoyl)-N-cyclopentylglycine

N,N¹-Dicyclohexylcarbodiimide (3.1 g, 15 mmol) in methylene chloride (50 ml) was added to 2-acetylthio-3-trifluoromethylbenzoic acid (4.0 g, 15 mmol) and N-cyclopentylglycine t-butyl ester (3.0 g, 15 mmol) in methylene chloride (200 ml) at 0° C. After stirring overnight, the mixture was filtered, the filtrate washed successively with dilute hydrochloric acid, saturated sodium bicarbonate solutiion, and brine, then dried and concentrated to a yellow oil.

The crude ester was dissolved in acetonitrile (20 ml), the solution was filtered and sodium iodide (3.4 g, 22 mmol) was added. After warming the mixture to 50°, chlorotrimethylsilane (2.4 g, 22 mmol) was introduced and heating was continued for 30 minutes. Water was added, the organic phase was removed and washed with sodium thiosulfate solution and brine, then concentrated. The residue was treated with aqueous sodium bicarbonate and, after washing with ethyl acetate, the aqueous portion was acidified to yield a brown gum. Column chromatographic purification gave the product as an amorphous solid.

Example IV

N-(2-Mercapto-3-trifluoromethylbenzoyl)-N-cyclopentylglycine

N-(2-Acetylthio-3-trifluoromethylbenzoyl)-N-cyclopentylglycine (1.4 g, 3.6 mmol) and 1 N sodium hydroxide solution were stirred 4 hours at room temperature, then acidified with concentrated hydrochloric acid and extracted with ethyl acetate. The organics were washed with water and brine, then dried and concentrated to a yellow gum which solidified on standing. Recrystallization from hexane/ethyl acetate gave a white solid, m.p. 144°–146° C.

Example V

A. 2-Mercapto-3-methylbenzoic acid

A slurry of 2-amino-3-methylbenzoic acid (30 g, 0.20 m) in water (100 ml) containing concentrated hydrochloric acid (70 ml) was treated dropwise at 0°–5° with sodium nitrite (13.8 g, 0.20 m) in water (56 ml). The resulting solution was slowly added at 0° to sodium sulfide nonahydrate (52 g, 0.22 m), sulfur (6.7 g, 0.21 m) and sodium hydroxide (7.8 g, 0.20 m) combined in water (70 ml). Excess sodium hydroxide was introduced near the end of the addition to keep the mixture basic. After stirring overnight the mixture was filtered and acidified to yield a brown semi-solid. This material and aqueous sodium carbonate were combined and filtered and the filtrate was acidified to provide the solid disulfide.

The crude product, zinc (15 g, 0.23 m) and glacial acetic acid (200 ml) were refluxed 4 hours, with additional zinc (15 g, 0.2 m) and acetic acid (100 ml) being added after the first hour. The mixture was cooled and filtered, the filter cake was extracted with dilute sodium hydroxide solution and the extracts were acidified to provide the crystalline product, m.p. 160°–162° C.

B. 2-Acetylthio-3-methylbenzoic acid

2-Mercapto-3-methylbenzoic acid (9.0 g, 54 mmol), acetic anhydride (6.5 g, 63 mmol) and glacial acetic acid (25 ml) were refluxed 1 hour, then poured into dilute hydrochloric acid. The product was filtered and recrystallized from toluene.

C. N-(2-Acetylthio-3-methylbenzoyl)-N-cyclopentylglycine t-butyl ester

N-Cyclopentylglycine t-butyl ester (8.3 g, 0.042 mole) and 2-acetylthio-3-methylbenzoic acid (8.9 g, 0.042 mole) were combined in 90 ml CH₂Cl₂. This solution was cooled to 0° C. before adding to it a solution of N,N-dicyclohexylcarbodiimide (8.6 g, 0.042 mole) in 30 ml $CH_2Cl_2$ dropwise over 15 minutes. The reaction was allowed to warm slowly to room temperature overnight.

The DCC-urea was then filtered and washed with $CH_2Cl_2$. The filtrate was washed 2×100 ml 1 N HCl, 2×100 ml saturated $NaHCO_3$ and 2×100 ml brine. The organic extract was then dried ($MgSO_4$), filtered and concentrated in vacuo to yield 16.7 g of a dark oil which was used without purification in the next step.

D. N-(2-Acetylthio-3-methylbenzoyl)-N-cyclopentylglycine

N-(2-Acetylthio-3-methylbenzoyl)-N-cyclopentylglycine t-butyl ester (16.7 g, 0.047 mole) was dissolved in 100 ml $CH_3CN$. Sodium iodide (9.6 g, 0.064 mole) was then added. The resulting slurry was covered with a nitrogen atmosphere and warmed slowly to 55° C. Chlorotrimethylsilane (6.9 g, 0.0641 mole) was then added in one portion. The reaction was stirred 30 minutes at 50°–55° C. The heat source was then removed and the reaction cooled to room temperature with an ice bath. Water (60 ml) and $CH_2Cl_2$ (100 ml) were then added. The reaction mixture was transferred to a separatory funnel and the aqueous layer quickly withdrawn. The organic was washed 2×50 ml $H_2O$, 3×75 ml $Na_2S_2O_3$, 2×100 ml brine, dried ($MgSO_4$), filtered and concentrated in vacuo to give 15.9 g of an orange oil.

The oil was then dissolved in saturated $NaHCO_3$. The alkaline solution was washed 2×100 ml ethyl acetate and the organic extracts discarded. The alkaline solution was then acidified with concentrated HCl and washed 3×100 ml $CH_2Cl_2$. The combined organic extracts were dried ($MgSO_4$), filtered and concentrated to yield 5.1 g (0.015 mole) of an oil which later solidified. This material was recrystallized from hexane:ethyl acetate (1:1), m.p. 122°–124° C.

Example VI

N-(2-Mercapto-3-methylbenzoyl)-N-cyclopentylglycine

To a chilled solution of methanolic ammonia (30 ml) was added 2.6 g (0.0078 mole) of N-(2-acetylthio-3-methylbenzoyl)-N-cyclopentylglycine. The reaction was covered with a nitrogen atmosphere and stirred three hours while warming slowly from 0° C. to room temperature.

The clear, yellow solution was concentrated in vacuo. The crude material was dissolved in ethyl acetate (50 ml) and washed 2×30 ml 1 N HCl and 2×50 ml brine. The organic layer was dried ($MgSO_4$), filtered and concentrated to give 2.3 g (0.0078 mole) of an oil which later solidified. This material was chromatographed on a silica gel column using n-hexane:ethyl acetate:acetic acid (5:5:0.3) as the eluent. The appropriate fractions were combined and recrystallized from hexane:ethyl acetate (1:1), m.p. 117°–119° C.

Example VII

A. 3-Chloro-2-aminobenzoic acid

Sodium dithionite (104.4 g, 0.6 m) in water (400 ml) was added in portions to a slurry of 3-chloro-2-nitrobenzoic acid (30 g, 0.15 m) in water (200 ml) containing concentrated ammonium hydroxide solution (10 ml). After stirring an additional 20 minutes the mixture was filtered, acidified to pH 3–4 with concentrated hydrochloric acid and filtered again. The filtrate was saturated with sodium chloride and extracted with ether. Drying and concentration of the extract gave a white powder which was combined with the precipitates above. The crude product was used without further purification.

B. Di(2-Chloro-6-carboxyphenyl)disulfide

Sodium nitrite (6.9 g, 0.10 m) in water (30 ml) at 0° C. was added in one portion to a slurry of 3-chloro-2-aminobenzoic acid (17.2 g, 0.10 m) in concentrated hydrochloric acid (20 ml)/water (50 ml) containing crushed ice. The mixture was shaken vigorously for several minutes, then filtered. The cold filtrate was slowly added at 0° to a solution of sodium sulfide nonahydrate (26 g, 0.11 m), sulfur (3.4 g, 0.11 m), sodium hydroxide (4.0 g, 0.10 m) and water (40 ml). The mixture was brought to room temperature over several hours, filtered and acidified (concentrated hydrochloric acid) and the disulfide collected by filtration.

C. 3-Chloro-2-mercaptobenzoic acid

Di-(2-Chloro-6-carboxyphenyl)disulfide (13.4 g, 35.7 mmol), zinc (7.5 g, 115 mmol) and glacial acetic acid (150 ml) were refluxed one hour; more zinc (7.5 g, 115 mmol) was added, and reflux was continued an additional 3 hours. The mixture was cooled and filtered and the precipitate extracted with hot dilute sodium hydroxide solution. Acidification of the extract (concentrated hydrochloric acid) gave the solid product.

D. 2-Acetylthio-3-chlorobenzoic acid

3-Chloro-2-mercaptobenzoic acid (9.8 g, 52 mmol), acetic anhydride (6.3 g, 62 mmol) and glacial acetic acid (22 ml) were heated at 80° C. for 4 hours, then cooled and mixed with dilute hydrochloric acid. The crystalline product was filtered.

E. N-(2-Acetylthio-3-chlorobenzoyl)-N-cyclopentylglycine t-butyl ester

2-Acetylthio-3-chlorobenzoic acid (11.5 g, 50 mmol) and N-cyclopentylglycine t-butyl ester (10.0 g, 50 mmol) in methylene chloride (350 ml) were cooled to 0°–5° C., and $N,N^1$-dicyclohexylcarbodiimide (10.3 g, 50 mmol) in methylene chloride (50 ml) was added. The mixture was stirred overnight. The DCC-urea was filtered and washed with $CH_2Cl_2$. The filtrate was then washed 2×125 ml 1 N HCl, 2×125 ml saturated $NaHCO_3$, 2×125 ml brine, dried ($MgSO_4$), filtered and concentrated to give 20.6 g of an oil. The crude product was used without further purification in the next step.

Example VII

N-(2-Acetylthio-3-chlorobenzoyl)-N-cyclopentylglycine

N-(2-Acetylthio-3-chlorobenzoyl)-N-cyclopentylglycine t-butyl ester (20.6 g, 0.05 mole) was dissolved in 150 ml $CH_3CN$. Sodium iodide (11.3 g, 0.075 m) was then added. The resulting slurry was covered with nitrogen and warmed to 55° C. Chlorotrimethylsilane (8.15 g, 0.075 m) was then added in one portion. The reaction was stirred 30 minutes at 55° C. under nitrogen atmosphere. The heat source was removed and the reaction cooled to room temperature in an ice bath. Water (60 ml) and $CH_2Cl_2$ (100 ml) were then added. The aqueous layer was quickly withdrawn and the organic layer washed 2×75 ml $H_2O$, 2×75 ml $Na_2S_2O_3$ and 2×75 ml brine. The organic layer was then dried ($MgSO_4$), filtered and concentrated to yield a dark yellow oil.

The oil was dissolved in saturated $NaHCO_3$. The alkaline solution was washed 3×100 ml ethyl acetate. The organic extracts were discarded and the alkaline solution acidified with concentrated HCl. The acidic solution was washed 4×200 ml CH$_2$Cl$_2$, the organic extracts combined, dried (MgSO$_4$), filtered and concentrated to yield 11.2 g (0.032 mole) of an oil which did not crystallize.

Further purification was done using a 12"×1½" silica gel column and eluting with hexane:ethylacetate:acetic acid (5:5:0.3). This afforded 7.4 g of a glassy material. On repeated washing with refluxing hexane this provided an amorphous solid.

Example VIII

N-(2-Mercapto-3-chlorobenzoyl)-N-cyclopentylglycine

To a chilled solution of methanolic ammonia (50 ml) was added 3.7 g (0.0104 m) of N-(2-acetylthio-3-chlorobenzoyl)-N-cyclopentylglycine. The reaction was covered with nitrogen and stirred 3 hours while warming slowly from 0° C. to room temperature.

The clear, yellow solution was concentrated in vacuo. The crude material was dissolved in ethyl acetate and washed 2×50 ml 1 N HCl, 2×50 ml brine, dried (MgSO$_4$), filtered and concentrated to yield 3.0 g (0.0095 m) of an oil which later solidified. This material was recrystallized from hexane:ethyl acetate (1:1), m.p. 141°–142° C.

Example IX

A. 2-Amino-3-methoxybenzoic acid

Sodium dithionite (84 g, 0.48 m) in water (100 ml) was added to 2-nitro-3-methoxybenzoic acid (20 g, 0.10 m) in water (100 ml)/concentrated ammonium hydroxide solution (6 ml). After stirring 3 hours the product was filtered. Acidification of the filtrate, saturation with sodium chloride and extraction with ether provided a small second crop of product.

B. 2-Mercapto-3-methoxybenzoic acid

A slurry of 2-amino-3-methoxybenzoic acid (22.3 g, 0.133 m) in water (66 ml)/concentrated hydrochloric acid (27 ml) was diazotized at 0° with sodium nitrite (9.3 g, 0.135 m) in water (37 ml). The supernatant liquid was decanted from insoluble matter and added at 0° to a mixture of sulfur (4.5 g, 0.14 m), sodium sulfide nonahydrate (34.7 g, 0.144 m) and sodium hydroxide (5.2 g, 0.13 m) in water (47 ml). After two days the mixture was filtered and acidified to yield the solid disulfide.

The moist product, zinc (10 g, 0.15 m) and glacial acetic acid (200 ml) were refluxed 1 hour, a second portion of zinc (10 g, 0.15 m) was added and reflux was continued for 3 hours. After cooling, the precipitate was filtered and extracted with dilute sodium hydroxide solution. The basic extract was acidified and the solid product collected.

C. 2-Acetylthio-3-methoxybenzoic acid

A solution of 2-mercapto-3-methoxybenzoic acid (14.6 g, 79 mmol), acetic anhydride (9.7 g, 95 mmol) and glacial acetic acid (35 ml) was refluxed 15 minutes, then cooled and poured into dilute hydrochloric acid. The product was vacuum-filtered.

D. N-(2-Acetylthio-3-methoxybenzoyl)-N-cyclopentylglycine

N,N$^1$-Dicyclohexylcarbodiimide (10.3 g, 50 mmol) in methylene chloride (80 ml) was added to 2-acetylthio-3-methoxybenzoic acid (11.3 g, 50 mmol) and N-cyclopentylglycine t-butyl ester (10.0 g, 50 mmol) in methylene chloride (300 ml) at 0°–5° C. Overnight stirring was followed by filtration and washing of the filtrate with dilute hydrochloric acid, sodium bicarbonate solution and brine. Drying and concentration gave a gum which was dissolved in acetonitrile (65 ml), combined with sodium iodide (11.2 g, 75 mmol) and heated to 40°–50° C. Chlorotrimethylsilane (8.1 g, 75 mmol) was introduced and the mixture was heated for 30 minutes, then quenched with water. The organic phase was washed with water, aqueous sodium thiosulfate and brine then concentrated. Aqueous sodium bicarbonate was added to the residue and the resulting solution was washed with methylene chloride and ether, then acidified and extracted with ethyl acetate. The organic portion was dried and concentrated and the residue passed through a silica gel column to provide the amorphous product.

Example X

N-(2-Mercapto-3-methoxybenzoyl)-N-cyclopentylglycine

N-(2-Acetylthio-3-methoxybenzoyl)-N-cyclopentylglycine (4.4 g, 12.5 mmol) was stirred with excess sodium hydroxide solution for 2 hours at 25° C., then acidified and extracted with ethyl acetate. The extract was washed with water and brine, then dried and concentrated. The amorphous product was obtained by column chromatography of the residue.

Example XI

N-(3-Chlorosalicyloyl)-N-cyclopentylglycine

3-Chloroacetylsalicylic acid was combined with N-cyclopentylglycine t-butyl ester and N,N$^1$-dicyclohexylcarbodiimide at 0° C. in methylene chloride as described in Example I. Similar workup gave crude N-(3-chloroacetylsalicyloyl)-N-cyclopentylglycine t-butyl ester, which was cleaved to N-(3-chloroacetylsalicyloyl)-N-cyclopentylglycine using iodotrimethylsilane prepared in situ as described in Example I. Hydrolysis with aqueous sodium hydroxide (Example IV) provided the title compound.

Example XII

N-Anthraniloyl-N-cyclopentylglycine

N-Acetylanthranilic acid, N-cyclopentylglycine t-butyl ester and N,N$^1$-dicyclohexylcarbodiimide were reacted in methylene chloride at 0° as described in Example I. Workup provided N-(N$^1$-acetylanthraniloyl)-N-cyclopentylglycine t-butyl ester, which on treatment with chlorotrimethylsilane/sodium iodide (Example 1) gave N-(N$^1$-acetylanthraniloyl)-N-cyclopentylglycine. Hydrolysis of the N-acetate furnished the desired amino acid.

By using the procedures described in the above example, the following additional compounds were prepared:

N-(3-acetylthiobenzoyl)-N-cyclopentylglycine
N-(4-acetylthiobenzoyl)-N-cyclopentylglycine
N-(3-chloro-2-trimethylacetylthiobenzoyl)-N-cyclopentylglycine
N-(3-methoxy-2-trimethylacetylthiobenzoyl)-N-cyclopentylglycine
N-(2-mercaptobenzoyl)-L-proline
N-(4-acetyl-2-acetylthiobenzoyl)-N-cyclopentylglycine
N-salicyloyl-N-cyclopentylglycine
N-(N$^1$-acetylanthraniloyl)-N-cyclopentylglycine
N-(2-acetylthio-4-methylsulfoxylbenzoyl)-N-cyclopentylglycine
N-(2-acetylthio-4-methylsulfonylbenzoyl)-N-cyclopentylglycine
N-(2-acetylthio-5-sulfamylbenzoyl)-N-cyclopentylglycine N-(2-acetylthio-3,5-dimethoxybenzoyl)-N-cyclopentylglycine N-(2-acetylthio-3,5-dichlorobenzoyl)-N-cyclopentylglycine N-(2-acetylthiobenzoyl)-N-(p-tolyl)glycine N-(2-acetylthio-5-aminobenzoyl)-N-cyclopentylglycine N-(2-acetylthio-4-dimethylaminobenzoyl)-N-cyclopentylglycine N-(2-acetylthio-5-carboxybenzoyl)-N-cyclopentylglycine N-(2-acetylthio-4-chloro-5-sulfamylbenzoyl)-N-cyclopentylglycine N-(2-mercapto-3-chloro-6-hydroxybenzoyl)-N-cyclopentylglycine N-(2-acetylthio-3-chloro-5-acetylbenzoyl)-N-cyclobutylglycine The compounds of the present invention have demonstrated potent activity (of the order of 0.75 to 5 micromols) in inhibiting angiotensin converting enzyme (ACEI activity) when tested by the method described in Science 196, 441–4 (1977). As such, these compounds would be very useful in the treatment of hypertension. Administration of the compounds to hypertensive rats at dosage range of about 1.5 mg/kg decreased the blood pressure by about 5 to 25% for periods of about 4 to 10 hours. The compounds may be administered orally or parenterally in the treatment of hypertension, and it will be within the skill of the practitioner to determine the exact amount to be administered and the mode of administration.

We claim:

1. A compound of the structure

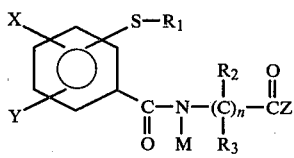

wherein:

X and Y are hydrogen, halogen, hydroxy, alkoxy, trifluoromethyl, nitro, carboxy, cyano, sulfonamido, sulfhydryl, alkyl, alkenyl, alkynyl, alkanoyl, alkylmercapto, amino, alkylamino, dialkylamino, and may be the same or different with the proviso that when X is nitro, sulfonamido, alkyl, alkenyl, or alkynyl Y is hydrogen, halo or trifluoromethyl;

$R_1$ is hydrogen, alkanoyl, substituted alkanoyl wherein the substituent is hydroxy, amino or cycloalkyl, benzoyl, phenylalkanoyl, or cycloalkylcarbonyl;

n is an integer from 1 to 4 inclusive;

$R_2$ and $R_3$ are hydrogen, alkyl, alkenyl, alkynyl, cycloalkyl, cycloalkyl-alkyl, phenyl, phenylalkyl, and substituted derivatives thereof wherein the substituents are hydroxy, amino, halogen, mercapto, alkylmercapto, and may be the same or different;

M is alkyl, alkenyl, alkynyl, cycloalkyl, cycloalkylalkyl, phenyl or phenylalkyl; and Z is hydroxy, amino, alkylamino, dialkylamino, or alkoxy, wherein the alkyl, alkenyl, and alkynyl groups and the alkyl moieties in alkoxy, alkanoyl, alkylmercapto, alkylamino, and dialkylamino contain from 1 to 6 carbon atoms, the cycloalkyl groups contain from 3 to 7 carbon atoms, and where Z is hydroxy, their pharmaceutically acceptable, nontoxic alkali and alkaline earth salts.

2. A compound according to claim 1 wherein X is hydrogen.

3. A compound according to claim 2 wherein Z is hydroxy.

4. A compound according to claim 3 wherein n is 1.

5. A compound according to claim 4 wherein $R_1$ is hydrogen.

6. A compound according to claim 5 wherein Y is hydrogen, methyl, chloro, trifluoromethyl or methoxy.

7. A compound according to claim 4 wherein $R_1$ is acetyl.

8. A compound according to claim 7 wherein Y is hydrogen, methyl, chloro, trifluoromethyl or methoxy.

9. A compound of the structure

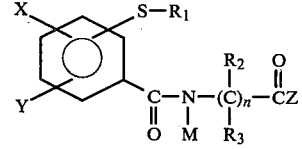

wherein:

X is H;

Y is at the 3 position and is hydrogen, methyl, chloro, trifluoromethyl or methoxy, $R_1$ is hydrogen or acetyl, n is 1, and M is a $C_3$–$C_7$ cycloalkyl.

10. A compound of the structure

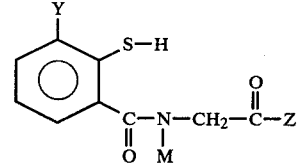

wherein

Y is hydrogen, methyl, chloro, trifluoromethyl or methoxy,

M is a $C_3$–$C_7$ cycloalkyl,

Z is hydroxy and their pharmaceutically acceptable, nontoxic alkali, and alkaline earth salts.

11. The compound of claim 10 wherein Y is chloro and M is cyclopentyl.

12. The compound of claim 10 wherein Y is methoxy and M is cyclopentyl.

* * * * *